(12) United States Patent
De Groot

(10) Patent No.: US 10,234,438 B2
(45) Date of Patent: Mar. 19, 2019

(54) DEVICE AND METHOD FOR MEASURING PLANT GROWTH CONDITIONS

(71) Applicant: Rockwool International A/S, Hedehusene (DK)

(72) Inventor: Jacob Frank De Groot, Roermond (NL)

(73) Assignee: ROCKWOOL INTERNATIONAL A/S (DK)

( * ) Notice: Subject to any disclaimer, the term of this patent is extended or adjusted under 35 U.S.C. 154(b) by 832 days.

(21) Appl. No.: 14/765,025

(22) PCT Filed: Feb. 7, 2014

(86) PCT No.: PCT/EP2014/052475
§ 371 (c)(1),
(2) Date: Jul. 31, 2015

(87) PCT Pub. No.: WO2014/122284
PCT Pub. Date: Aug. 14, 2014

(65) Prior Publication Data
US 2015/0369786 A1    Dec. 24, 2015

(30) Foreign Application Priority Data

Feb. 8, 2013 (EP) ..................................... 13154643
Jun. 26, 2013 (GB) ..................................... 1311343.6

(51) Int. Cl.
*G01N 33/00* (2006.01)
*A01G 25/16* (2006.01)
(Continued)

(52) U.S. Cl.
CPC ....... *G01N 33/0098* (2013.01); *A01G 25/167* (2013.01); *A01G 31/02* (2013.01);
(Continued)

(58) Field of Classification Search
CPC ........ G01N 22/00; G01N 22/04; G01N 24/00; G01N 24/08; G01N 24/081; G01N 27/00;
(Continued)

(56) References Cited

U.S. PATENT DOCUMENTS

| 5,107,621 A * | 4/1992 | Deutschmann, Sr. ....................... A01G 27/008 47/59 R |
| 2003/0000573 A1 * | 1/2003 | Yoshioka ............. A01G 27/003 137/78.3 |

(Continued)

FOREIGN PATENT DOCUMENTS

| EP | 0392639 | 10/1990 |
| JP | 2011-13025 | 1/2011 |

(Continued)

OTHER PUBLICATIONS

Australian Examination Report dated Jul. 12, 2017 for corresponding AU Application No. 2014213963.
(Continued)

*Primary Examiner* — Hoai-An D. Nguyen
(74) *Attorney, Agent, or Firm* — Tarolli, Sundheim, Covell & Tummino LLP

(57) ABSTRACT

A device (10) and method are provided for measuring the plant growth conditions within a substrate. A first and a second linear arrays of probes (16, 18) are used, allowing multiple measurements of properties of the substrate. Using multiple measurements at different levels in the substrate and then combining these multiple measurements, allows plant growth conditions to be accurately derived.

23 Claims, 9 Drawing Sheets

(51) Int. Cl.
*A01G 31/02* (2006.01)
*G01N 27/02* (2006.01)
*G01N 27/04* (2006.01)
*G01N 27/22* (2006.01)
*A01G 24/18* (2018.01)

(52) U.S. Cl.
CPC ......... *G01N 27/028* (2013.01); *G01N 27/041* (2013.01); *G01N 27/223* (2013.01); *A01G 24/18* (2018.02); *Y02P 60/216* (2015.11)

(58) Field of Classification Search
CPC ...... G01N 27/02; G01N 27/028; G01N 27/04; G01N 27/041; G01N 27/043; G01N 27/045; G01N 27/048; G01N 27/223; G01N 33/00; G01N 33/0098; A01G 24/00; A01G 24/18; A01G 25/00; A01G 25/16; A01G 25/167; A01G 31/00; A01G 31/02; Y02P 60/00; Y02P 60/216
USPC ....... 324/600, 629, 633, 634, 637, 639, 640, 324/642, 643, 649, 658, 663, 664, 686, 324/689, 691, 693, 694, 696, 76.11, 96; 73/73
See application file for complete search history.

(56) References Cited

U.S. PATENT DOCUMENTS

2008/0093549 A1\* 4/2008 Haigh .................. G01N 27/622 250/288

2011/0273196 A1 11/2011 Hill
2012/0156692 A1\* 6/2012 Sasaki ..................... A01G 7/00 435/7.4
2014/0075838 A1\* 3/2014 Limbrunner ......... A01B 79/005 47/58.1 R

FOREIGN PATENT DOCUMENTS

SU 1336997 A1 9/1987
WO 2010031773 3/2010

OTHER PUBLICATIONS

Australian Examination Report dated Dec. 21, 2016 for corresponding AU Application No. 2014213963.
Chinese Office Action dated Sep. 5, 2016 for corresponding CN Application No. 201480007734.0.
Chinese Office Action dated May 15, 2017 for corresponding CN Application No. 201480007734.0.
Japanese Office Action dated Apr. 26, 2017 for corresponding JP Application No. 2015-556515.
Russian Office Action dated Jan. 24, 2017 for corresponding RU Application No. 2412-527238.
Soil and Fertilizer Analysis, Chinese Academy of Agricultural Sciences, Jiangsu Branch, pp. 116-117, Shanghai Science and Technology Press, Sep. 1960, with English translation.
International Search Report to PCT International Appl. No. PCT/EP2014/052475, 2 pages.

\* cited by examiner

DEVICE AND METHOD FOR MEASURING PLANT GROWTH CONDITIONS

FIELD OF THE INVENTION

The present invention relates to the detection of plant growth conditions within plant growth substrates. In particular, but not exclusively, the present invention relates to devices designed for use with artificial plant growth substrates, such as mineral wool substrates.

BACKGROUND TO THE INVENTION

In recent years, the management and steering of plant growth has become increasingly specialised and closely managed. Whereas irrigation strategies were once applied field-wide with a general aim merely to compensate for lack of rainwater, plants are increasingly fed water in small groups or even individually with the aim of carefully controlling plant growth conditions.

For example, it is recognised that irrigation strategies can have a qualitative effect on the growth of plants. As is understood in the art, generative growth refers to a type of growth in which the production of flowers/fruit is encouraged, while during vegetative growth the plant a higher proportion of leaves and other green elements are produced. Generative growth is encouraged when a plant has a relative lack of water and/or nutrients, while vegetative growth is encouraged by a plentiful supply of water and/or nutrients. Vegetative growth produces the higher increase in overall biomass of the plant, while generative growth increases the proportion of the growth which contributes to the production of fruit or flowers.

It can therefore be seen that close control of plant growth conditions can be used to steer the type of growth towards a desired outcome. However, if control at this relatively fine level is to be achieved, then measurement of the plant growth conditions is critical.

One particular context in which such close control has been proposed is that of the growing of plants in mineral wool growth substrates. Such growth substrates are typically provided as a coherent plug, block, slab or mat/blanket and generally include a binder, usually an organic binder, in order to provide structural integrity to the product.

Typically, the growth process of the plant is managed in two stages: a first stage managed by a "propagator" in which the plant is grown from seed; and a second stage managed by a "grower" during which the plant is sustained and any harvest taken. For example, in the case of the tomato plant, the propagator may plant individual tomato seeds in cylindrical plugs having a thickness in the order of 25-30 mm and a radius of around 20-30 mm. After germination of the seed, the propagator places the plug within a cuboid block to allow further growth of the root system and the plant. The individual plant within the block is then nursed until a stage when it can be transferred from the propagator to the grower.

After they are received from the propagator, the grower places a number of blocks on a single slab of mineral wool to form a plant growth system. The slab of mineral wool is typically encased in a foil or other liquid impermeable layer except for openings on an upper surface for receiving the blocks with the plants and a drain hole provided on the bottom surface.

During subsequent growth of the plant, water and nutrients are provided using drippers which deliver a liquid containing water and nutrients to the system either directly to the blocks or to the slabs. The water and nutrients in the blocks and slabs is taken up by the roots of the plants and the plants grow accordingly. Water and nutrients which are not taken up by the plant either remain in the substrate system or are drained through the drain hole. Drained water and/or nutrients may be disinfected and subsequently reused if appropriate.

It is desirable to provide sensors which can be used to sense the level of water and/or nutrients of plant growth systems of this type. Suitable sensors have been proposed, and some examples are described in International patent application WO 2010/031773. FIG. 1 of this document shows a prior art water content meter having three protruding probes which are inserted into a substrate in order to measure properties such as the water content. WO 2010/031773 also describes a method for measuring capacitance of the substrate (from which the water content can be inferred) by flat plate electrodes against the surface of the substrate, rather than by inserting probes within the body of the substrate. EP0392639 describes a sensor unit with twenty inner pins having four outer pins located therearound, for measuring moisture content in a substrate. US 2011/0273196 describes a wireless environmental sensor with three or six steel pins arranged to interface with the soil at multiple points to take a single measurement representing an average property of the soil located between the pins interfacing with the soil.

While these approaches find utility, there are limits on the information that can be obtained using such techniques. In particular, it will be understood that the water content and other properties are not homogenous throughout the substrate. That is to say, there will normally be a variation in such properties throughout the substrate. Accordingly, attempts to measure water content and nutrient level from an electrical response can be too limited or variable.

For example, it may be expected that the action of gravity will cause water to settle in the bottom region of the substrate, leading to increased water content in a lower region as compared to an upper region. Other effects may depend on the location of the drain hole, for example, or the point at which irrigation is applied.

The calculation is further complicated by the properties of the substrate itself. For example, in an attempt to increase the homogeneity of water content, it has been proposed to provide substrates formed of layers having differing densities. A higher density upper layer of the substrate can increase the relative water content in that region. Nevertheless, water content remains variable throughout the substrate, making a reliable a consistent assessment of overall conditions difficult.

Closer control of plant growth conditions demands improved measurement of those conditions. There is an increasing desire to assess such conditions accurately and reliably, in such a way that plant growth strategies which operate optimally can be developed.

SUMMARY OF THE INVENTION

According to a first aspect of the present invention, there is provided a device for detecting plant growth conditions within a plant growth substrate, the device comprising:
  a first linear array of one or more probes for insertion into the substrate;
  a second linear array of one or more probes for insertion into the substrate, wherein the second linear array is located at a fixed distance from the first linear array; and a control unit arranged to obtain a first measurement of at least one property of the substrate at a first substrate level from the first linear array of probes and a second measurement of the at least one property of the substrate at a second substrate level from the second linear array of probes, wherein the control unit is further arranged to combine the first and second measurements obtained at the first and second substrate levels to calculate at least one plant growth condition of the substrate as a function of the first and second measurements.

Unlike conventional sensors for use in detecting plant growth conditions, the device of the first aspect obtains multiple measurements of at least one property of the substrate. Two linear arrays of probes are provided at a fixed separation from one another, enabling the two measurements to be obtained at different locations within the substrate. By a 'linear' array of the probes it will be understood that the probes in one array are located at approximately the same distance from the probes forming the other array to thereby measure a property at a substrate level. As the relative positions of these locations are fixed (and corresponding to the distance between the two different levels in the substrate), the conditions within the substrate can be modelled from the two measurements in a predetermined manner, enabling a clearer and more accurate understanding of the plant growth conditions within the substrate to be established. Specifically, by taking two measurements at different depths in the substrate for example, an improved calculation of the true plant growth conditions can be achieved, as these conditions vary throughout the substrate, particularly in the vertical direction.

It may be possible to adjust the distance between the linear arrays between uses, before this distance is fixed during operation. However, in the preferred embodiment, the distance between the linear arrays is permanently fixed.

In preferred embodiments, each array comprises at least two probes. More preferably, the probes in each array comprise at least two electrodes. In this manner, an electrical signal can be applied to the substrate through the probes, enabling measurement of electrical properties. Alternative or additional properties that may be measured include temperature.

In preferred embodiments, the at least one plant growth condition comprises water content within the substrate. This level is preferably expressed as a percentage level of the required water content for full saturation of the substrate. In preferred embodiments, the at least one property comprises capacitance. This enables the water content to be calculated, since the water content affects the dielectric properties of the substrate and is therefore a function of the capacitance.

In preferred embodiments, the at least one plant growth condition comprises nutrient content. Nutrient content is a reflection of the proportion of ionic salts within the substrate. As such, in preferred embodiments the at least one property is conductivity since this reflects the proportion of ionic salts in the substrate.

Preferably, the at least one plant growth condition comprises both water content and nutrient content. Accordingly, both capacitance and conductivity can be measured. It will be understood that these properties can be obtained by investigating the complex impedance of the substrate.

In preferred embodiments, each array comprises three probes. In particular, two of these probes may be electrodes for measuring electrical properties such as conductivity or capacitance, while a third may be a temperature sensor for measuring the temperature of the substrate.

Preferably, the probes are rotationally asymmetric at a distal end. For example, the probes may be oblique truncated cylinders. By cutting the distal end of generally cylindrical probes through an oblique plane, a relatively sharp distal edge is established thereby assisting in the introduction of the probes into the substrate. The device can therefore be applied to the substrate with relative ease. Moreover, bunching of fibres within the substrates can be avoided in comparison with probes having a blunt end. This is beneficial since such bunching may have an effect on measured properties of the substrate.

Preferably, the probes have a non-uniform rotational orientation. If the rotational orientations of the probes are all aligned, this may cause the device to be deflected from its desired position as it is introduced into the substrate. By arranging the orientations of the probes in a non-uniform manner, this effect is substantially reduced. In preferred embodiments, the probes may be provided as pairs of opposite rotational orientation (i.e. having orientations rotated through 180 degrees) so that the net deflection caused by each pair is summed to zero.

In some preferred embodiments, the rotational orientation of each probe is aligned with respect to a central point located between the probes. For example, each probe may have the same relative orientation with respect to a radius drawn from the central point to the probe. In particular preferred embodiments, a truncated surface of each probe is orientated towards the central point.

Preferably, the device further comprises an antenna for transmitting signals to a base station. In this way, measurements and calculated conditions can be retrieved without physical inspection of the device or without the need to a physical connection. This is advantageous in anticipated commercial settings, in which large numbers of substrates are managed within a single area.

In preferred embodiments, the device further comprises a guide element adapted to engage with an edge of the substrate. This can help to ensure that the guide is located in a consistent position on the substrate, allowing more reliable comparison of measurements from different devices. Furthermore, since the position of the probes in the substrate can be understood not just relative to one another but within the substrate as a whole, the modelling of the substrate can be more closely defined. Preferably, the guide element is adapted to engage with a bottom edge of the substrate. Alternatively or additionally, the guide element may be adapted to engage with a top edge of the substrate. Accordingly, the relative positions of the probes relative to the bottom and/or top edge of the substrate can be understood.

The guide element may be connected to the device by adjustable retaining means. This can allow for adjustment of the relative positions of the guide element and the probes, so that a distance of the probes from an edge of the substrate may be reliably set and adjusted as required, for different sizes of substrate, or for different growth conditions or measurement requirements.

The adjustable retaining means may be adapted to retain the guide element at a plurality of selectable positions relative to the probes. This can allow one of a range of set distances of the guide element from the probes to be selected and set, so that repeatable measurements can be made at any of a number of set distances of the guide element from the probes.

The adjustable retaining means may comprise an array of main engagement points on one of a main body of the device and the guide element, and a set of corresponding guide element engagement points on the other of the main body and the guide element, for engaging a sub-set of the array of main engaging points. This can enable a simple construction of one part, with a single set of engaging points, while a more complex array of plural sets of engagement points can be provided in the other part of the device. This allows a simpler manufacture of one part, such as the guide element, and can confine the more complex features of the device to a single element—such as the main body of the device.

The device may further comprise at least one blanking element for engaging main engagement points which are not engaged by the guide element engagement points. This can prevent, water, dirt or dust or other unwanted substances from obstructing the engagement points which are un-used by the mounting of the guide element in a certain position. It can also prevent unwanted substances from entering a main body of the device via holes which may be provided as engagement points for the guide element.

According to a second aspect of the invention, there is provided a device for detecting plant growth conditions within a plant growth substrate, the device comprising:
  a first linear array of one or more probes for insertion into the substrate;
  a second linear array of one or more probes for insertion into the substrate, wherein the second linear array is located at a fixed distance from the first linear array;
  control means arranged to obtain a first measurement of at least one property of the substrate from the first linear array of probes and a second measurement of the at least one property from the second linear array of probes,
  wherein at least one plant growth condition of the substrate can be calculated using the first and second measurements;
  the device further comprising a guide element adapted to engage with an edge of the substrate, wherein the guide element is connected to the device by adjustable retaining means adapted to retain the guide element at a plurality of selectable positions relative to the probes.

According to a third aspect of the invention, there is provided a plant growth system, comprising: a plant growth substrate comprising a man-made vitreous fibre (MMVF) slab; and a device according to the first or second aspect. The plant growth substrate may comprise further elements such as an MMVF block placed upon the slab, and an MMVF plug placed within the block. Preferably, the system comprises one and only one block. Thus, the conditions of the substrate can be closely controlled for plants growing in a single block.

Preferably, the probes of the device extend through a side wall of the slab. The first and second linear arrays of probes are preferably separated in a vertical direction, meaning that the multiple measurements (from which the plant growth conditions can be calculated) are taken from more than one height in the slab.

According to a fourth aspect of the present invention, there is provided a method for detecting plant growth conditions within a plant growth substrate, comprising:
  inserting probes of a detection device into the substrate, wherein the probes are arranged in a first linear array and a second array, the first linear array and the second linear array being located at a fixed distance from one another;
  obtaining a first measurement of at least one property of the substrate at a first substrate level from the first linear array of probes and obtaining a second measurement of the at least one property at a first substrate level from the second linear array of probes;
  combining the first and second measurements obtained at the first and second substrate levels; and
  calculating at least one plant growth condition of the substrate using the combined first and second measurements.

According to the fourth aspect, multiple measurements are taken at a predetermined distance from one another, and these are then combined in the calculation of a plant growth condition of the substrate. By taking two measurements (preferably at different heights in the substrate), an improved calculation of the true plant growth conditions can be achieved, as these conditions vary throughout the substrate.

It will be understood that, where appropriate, preferred features of the first aspect can apply to the second, third, or fourth aspects of the invention.

BRIEF DESCRIPTION OF THE FIGURES

Embodiments of the present invention will now be described with reference to the accompanying drawings, in which.

DETAILED DESCRIPTION

Figure 1:
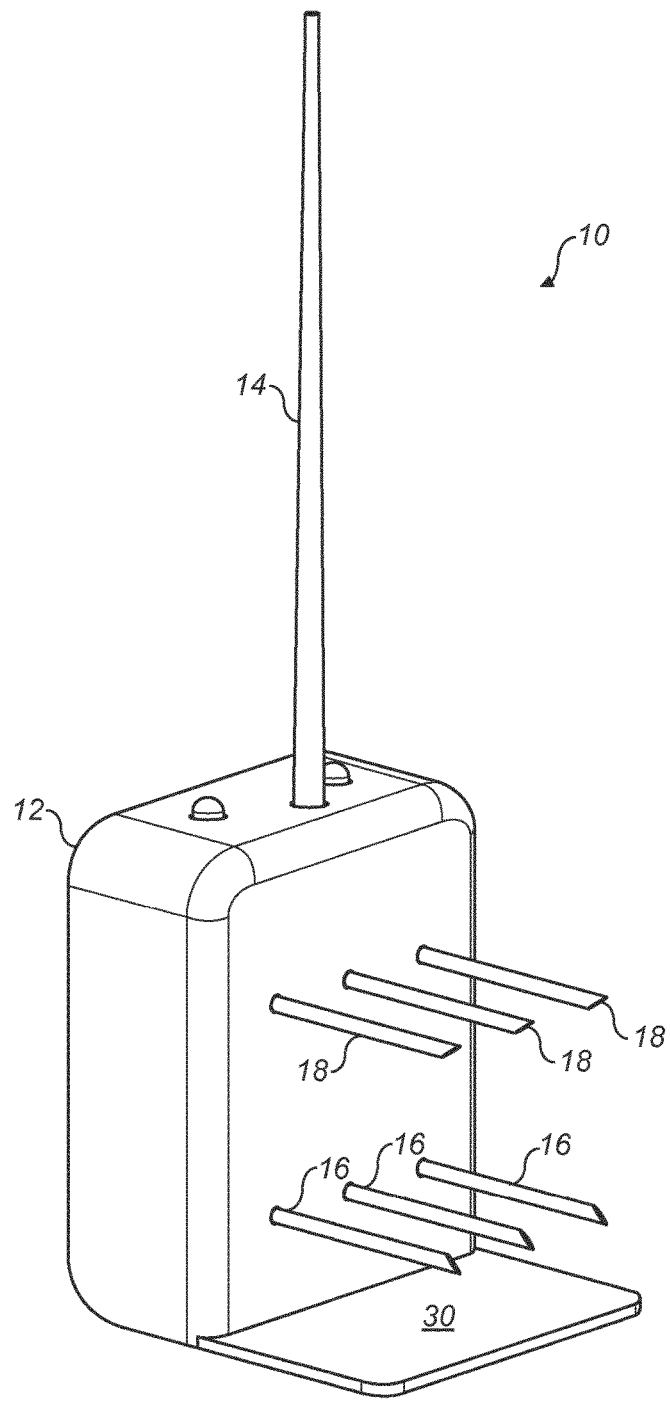
FIG. 1 shows a device for detecting plant growth conditions within a plant growth substrate according to a preferred embodiment of the present invention.

Referring to FIG. 1, a preferred embodiment of a device 10 for detecting plant growth conditions is shown. The device 10 comprises a body 12, an antenna 14, a first array of probes 16 and a second array of probes 18. Each array of probes 16, 18 are fixed to the body 12 of the device, meaning that the distance between the arrays is itself fixed.

The device 10 may further comprise additional features not shown in FIG. 1, such as a visible indicator (for example, a light emitting device (LED)) to indicate whether the device 10 is switched on or a user interface to allow the user to control the device 10. In a simple example, the control of the device may be limited to an on/off switch.

In the preferred embodiment shown in FIG. 1, each array of probes 16, 18 consists of three individual probes. In preferred embodiments, two of these may act as electrodes, with a third acting as a temperature sensor. The electrodes can be used to probe electrical properties of the substrate, such as the capacitance or conductivity of the substrate. The probes 16, 18 are preferably formed of stainless steel.

Each array of probes 16, 18 is a linear array, with the probes in the array being spaced at 25 mm intervals. In normal operation, the linear array extends in a horizontal direction. The linear arrays are displaced from one another by a pure vertical transformation, such that equivalent probes from each array are displaced directly above and below one another in normal use.

The first array 16 is preferably located around 25 mm from the bottom of the device 10, while the second array 18 is located at a position around 60 mm from the bottom of the device 10. Accordingly, in the preferred embodiment the second array 18 is around 35 mm above the first array 16. It is found that this separation is suitable for measurement of the plant growth conditions in the plant growth substrates of the type envisaged for use with the device 10. However, the skilled person will recognise that dimensions may vary for plant growth substrates of differing size.

Figure 2:
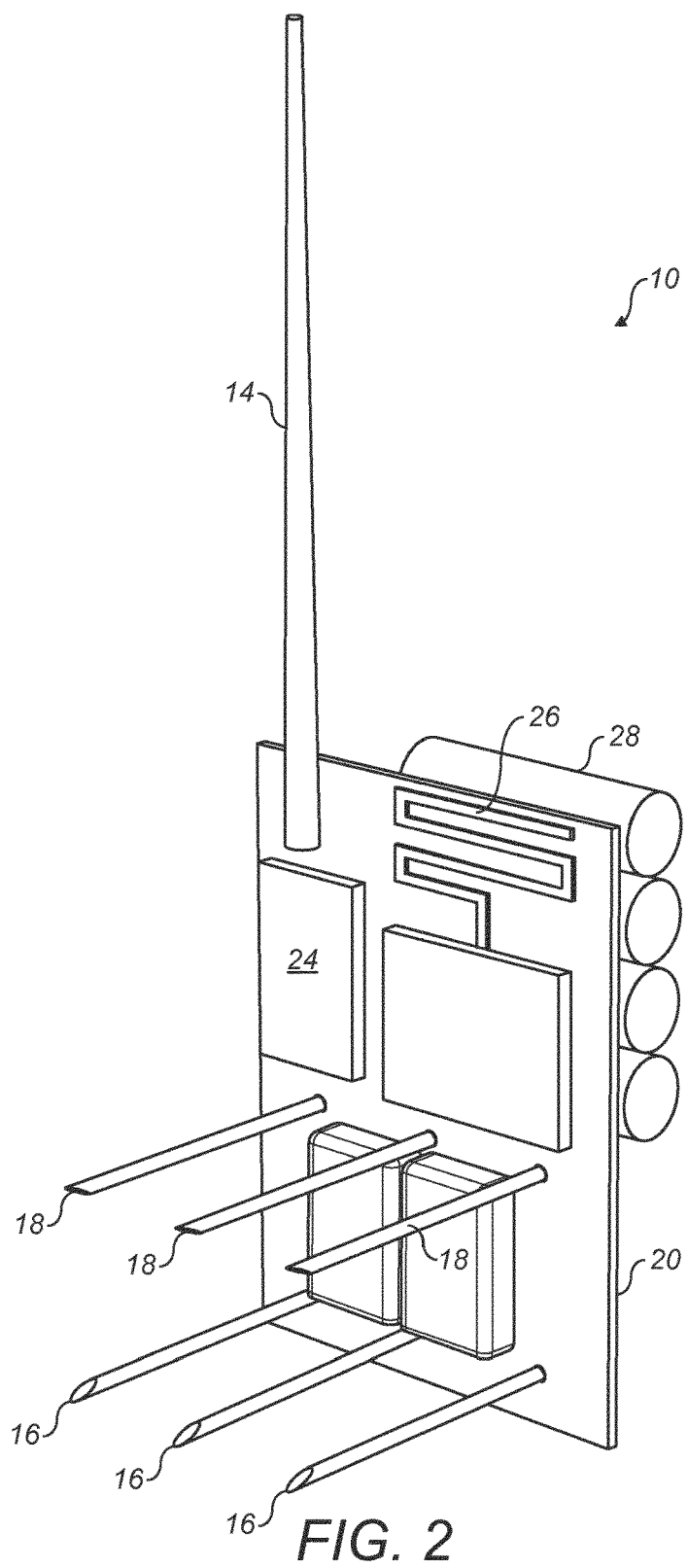
FIG. 2 shows internal feature of the device of FIG. 1.

FIG. 2 shows the device 10 without the body 12, thereby revealing the internal features of the device 10. As can be seen in FIG. 2, the device comprises a printed circuit board onto which the probes 16, 18 are mounted. Furthermore, the device comprises a control unit 22 also mounted to the printed circuit board 20. The control unit 22 is coupled to the probes 16, 18 via the printed circuit board and is arranged to obtain multiple measurements of the properties of a plant growth substrate from the probes. The control unit 22 may be arranged to apply an electrical signal to the one or more probes 16, 18 in order to obtain such measurements.

The device 10 further comprises radio module 24 for controlling antenna 14. The antenna 14 can be used to transmit measurements and/or calculated plant growth conditions to a base station. This allows such information to be collated from a number of similar devices in order to maintain control over a large system in which a plurality of plant growth substrates is provided. The radio module 24 and the antenna 14 may be connected through a short RF cable. In preferred embodiments, the antenna 14 transmits at a frequency of 868 MHz and is approximately 150 mm tall. As shown, the antenna 14 of the preferred embodiment is provided in a straight, non-articulated configuration. The skilled person will recognise that alternative antenna designs and frequencies of operation may be chosen as appropriate.

Indeed, in the preferred embodiment, an alternative radio system 26 is also shown. The alternative radio system 26 may, for example, transmit at a different frequency to the antenna 14 and radio module 24. It may be appropriate to have more than one option in a single device 10 to operate in accordance with varying local regulations regarding electromagnetic communications. For example, antenna 14 may be adapted for requirements within the European Union, while the alternative radio system 26 may be designed for use in the United States of America.

The device 10 further comprises a mounting for batteries 28. In the preferred embodiment, 4 AA batteries are used to provide power to the device.

Referring back to FIG. 1, it can further be seen that the device 10 comprises a guide element 30. The guide element 30 is arranged to engage with a bottom edge of the plant growth substrate. This has the effect of ensuring the arrays of probes 16, 18 are located at a predetermined distance from the bottom edge. In this manner, the position of the probes 16, 18 can be controlled. The guide element 30 of the preferred embodiment comprises a substantially planar protrusion which can be introduced underneath the plant growth substrate. Alternative configurations can be used as appropriate.

As mentioned above, in use the plant growth device 10 is engaged with a plant growth substrate. A plant growth system comprising the device 10 and a suitable substrate 50 is shown in FIG. 3.

Figure 3:
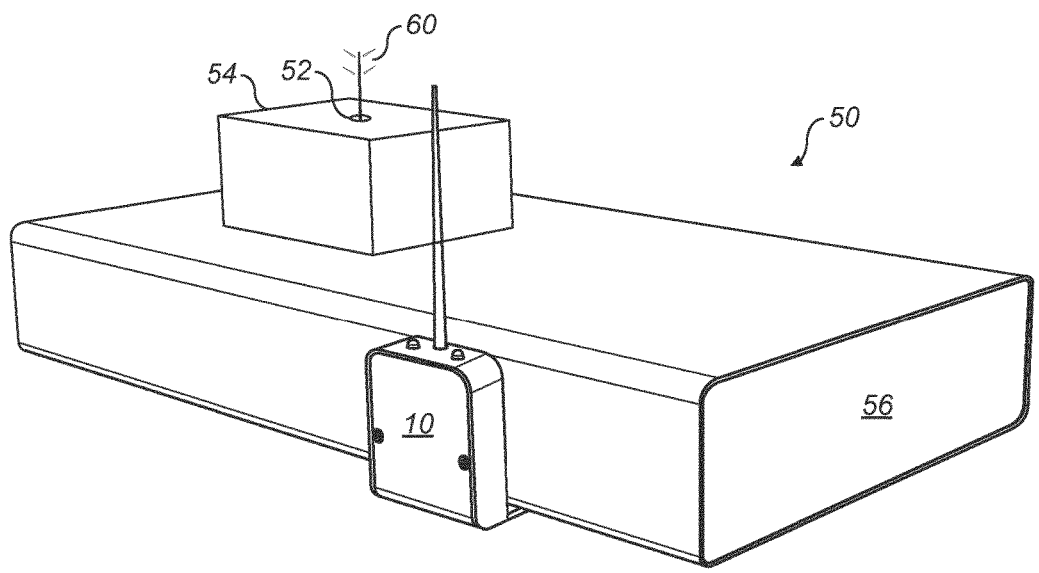
FIG. 3 shows a plant growth system comprising the device of FIG. 1 and a plant growth substrate.

In the system of FIG. 3, the plant growth substrate 50 comprises three elements: a plug 52, a block 54 and a slab 56. The plug 52 is disposed within the block 54 which is placed on an upper surface of the slab 56. FIG. 3 also shows a plant 60 growing from the substrate 50.

The plug 52 and the block 54 are used for early stage propagation of the plant 60 from seed. During the subsequent growth phase, the plug 52, block 54 and plant 60 are placed upon the slab 56. The system of FIG. 3 is used to measure properties of the substrate 50, particularly the slab 56, during this later growth phase. However, it will be understood that the invention may also find applicability during the earlier propagation phase.

The probes 16, 18 of the device 10 are pushed into the slab 56 to engage the device 10 with the plant growth substrate 50. The guide element 30 is abutted against the lower surface of the slab 56 to ensure that the heights of the probes 16, 18 are reliably defined.

The plug 52, block 54 and slab 56 are all preferably formed of man-made vitreous fibre (MMVF). Preferred MMVF may be fibre glass, mineral wool or refractory ceramic fibres. In the preferred embodiment, the MMVF is mineral wool, in particular stone wool. The plug 52, block 54 and slab 56 typically comprise a binder and/or wetting agent. Overall, the binder is preferably comprised in a hydrophilic binding system which may comprise the binder and a wetting agent, or may comprise the binder alone. By ensuring that the binding system is hydrophilic, the water retention properties of the slab can be improved relative to binding systems which are non-hydrophilic or hydrophobic. The present invention may also be used with non-MMVF substrates.

In the embodiment shown in FIG. 3, the height of the slab is 75 mm. In another preferred embodiment, the height of the slab 56 is 100 mm. The skilled person will recognise that alternative slab sizes can be used as appropriate. Preferably, the slab 56 is comprised of multiple horizontal layers of MMVF of differing densities. In particular, a higher density layer of MMVF may be disposed above a lower density layer of MMVF. The depths of the layers and the probes 16, 18 of the device are arranged such that the first array of probes 16 and the second array of probes 18 are disposed in different layers of the slab 56.

The device 10 is coupled to the substrate 50 by pushing the probes 16, 18 in to the side wall of the slab 56. The probes 16, 18 have a substantially cylindrical shape but are obliquely cut at a distal end. Thus, the probes 16, 18 are oblique truncated cylinders. The oblique truncation of the cylinders assists in the introduction of the probes 16, 18 into the slab 56, since it provides a sharp distal edge which can cut fibres within the slab 56 rather than simply bunching them together.

As a result of the oblique truncation of the distal end portions of the probes 16, 18, the probes 16, 18 are rotationally asymmetric. This rotational asymmetry means that as a probe is pushed into the slab 56 transversely, a lateral displacement force may become apparent. In the preferred embodiment of the invention, the probes 16, 18 are deliberately disposed at differing rotational orientations. This helps to avoid the possibility that the lateral displacement forces from each probe will constructively combine to cause misalignment of the device 10 as it is introduced into the slab 56.

Figure 4:
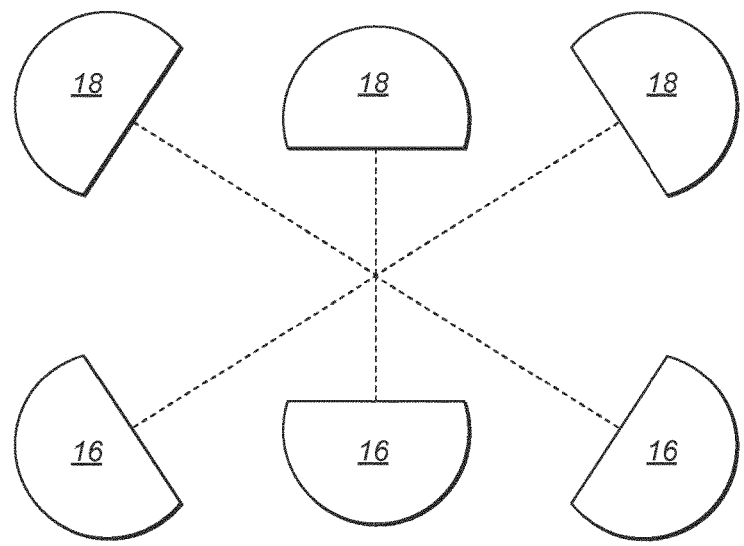
FIG. 4 illustrates the rotational orientation of the probes of the device of FIG. 1.

The above feature of the preferred embodiment is illustrated in FIG. 4, which shows cross sections of the probes 16, 18 in a region near the distal ends where the cylindrical profile is asymmetrically compromised by the oblique truncation plane of the probes 16, 18. In the preferred embodiment, pairs of the probes 16, 18 are disposed at opposite rotational orientations (i.e. are relatively rotated through 180 degrees). Moreover, each pair of probes contains one probe from the first array 16, and one probe from the second array 18. In FIG. 4, a first pair of probes comprises the top left and the bottom right probe, a second pair of probes comprises the top right and the bottom left probes and a third pair comprises the top middle and bottom middle probes. Pairs of probes are illustrated connected by dashed lines. The dashed lines also help to illustrate how in this embodiment, the rotational orientation of each probe is chosen relative to a central point (at the intersection of the dashed lines). Specifically, the truncated surface of each probe in this embodiment is orientated towards the central point. As the device 10 is pushed into the slab 56 the lateral force created by one probe from a pair is counteracted by the lateral force from the second probe in the pair leading to a net effect of zero.

In use, the device 10 is engaged with the plant growth substrate 50 as shown in FIG. 3. The plant growth substrate 50 is used to feed the plant 60 with water and/or nutrients by providing an irrigation device (not shown) which drips water and/or nutrients into the block 54 and/or slab 56. In order to control the actions of the irrigation device to ensure ideal plant growth conditions, it is desirable to measure those conditions in the slab 56.

The device 10 takes distinct measurements of properties of the slab from each array of probes 16, 18. These properties may include temperature and/or electrical properties such as electrical conductivity and capacitance. Temperature is itself a plant growth condition, whereas electrical conductivity and capacitance can be used to derive further plant growth conditions such as nutrient level (measured by proportion of ionic salts) and water content respectively.

Measurements from the probes 16, 18 reflect local conditions to those probes. In order to estimate the true overall conditions within the slab, the two measurements from each probe are combined in order to calculate the overall plant growth conditions. The relative weight given to each measurement and the manner in which they are combined can be chosen appropriately. For example, conditions within the slab as a function of the two measurements can be modelled using theoretical, empirical or semi-empirical techniques. The accuracy available by taking a plurality of measurements is significantly greater than that possible through a single measurement.

Figure 5:
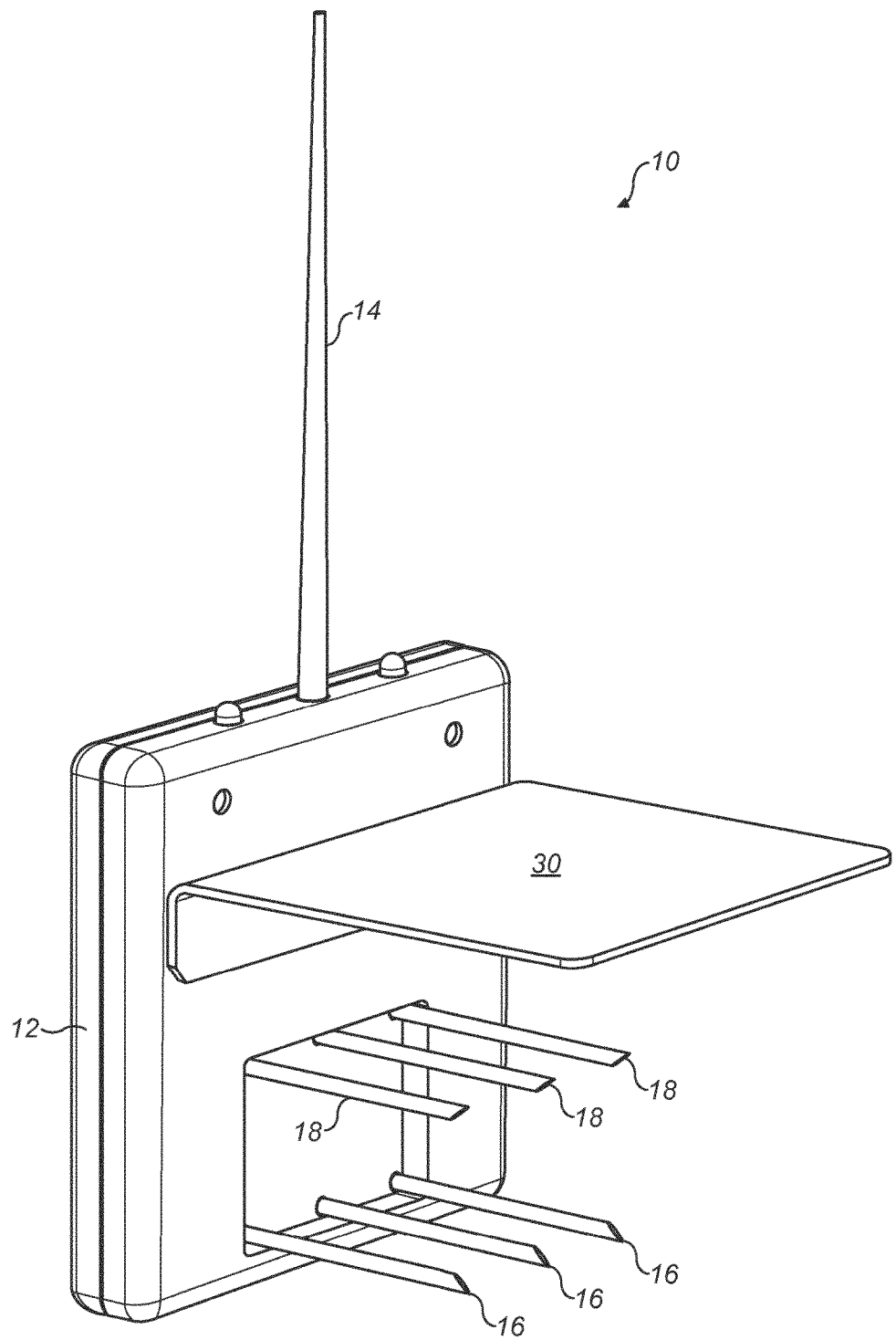
FIG. 5 illustrates an alternative embodiment of the present invention.

The present invention may take alternative forms to that shown in the preferred embodiment. For example, the guide element 30 may alternatively or additionally be designed to orientate the device 10 from the top edge of the slab 56 rather than the bottom edge as shown in the Figures above. For example, the alternative embodiment shown in FIG. 5 comprises a guide element 30 that is suitable to engage with the top edge of the slab 56. The embodiment shown in FIG. 5 is identical to that described with respect to the earlier figures except in the positioning of the guide element 30. The guide element 30 is positioned above the probes 16, 18 and may therefore be engaged with the top surface of the slab 56 when in use.

One advantage of a guide element that refers to the bottom edge of the slab is that it is found to offer greater applicability for the device across a range of slab 56 heights. Nevertheless, a guide element designed to reference the top edge of the slab may reduce interference in the slab arrangement. In some embodiments, the guide element 30 may be adjustable for positioning with slabs 56 of different heights, particularly when the guide element is to be used with the top edge of the slab 56. Different slab heights may be used for differing crops and, in certain arrangements, slabs may be placed in trays with a raised gutter, making setting a distance from a bottom of the slab impractical. A number of distances of a guide element from probes of a device of the invention may therefore be beneficial.

Figure 6A:
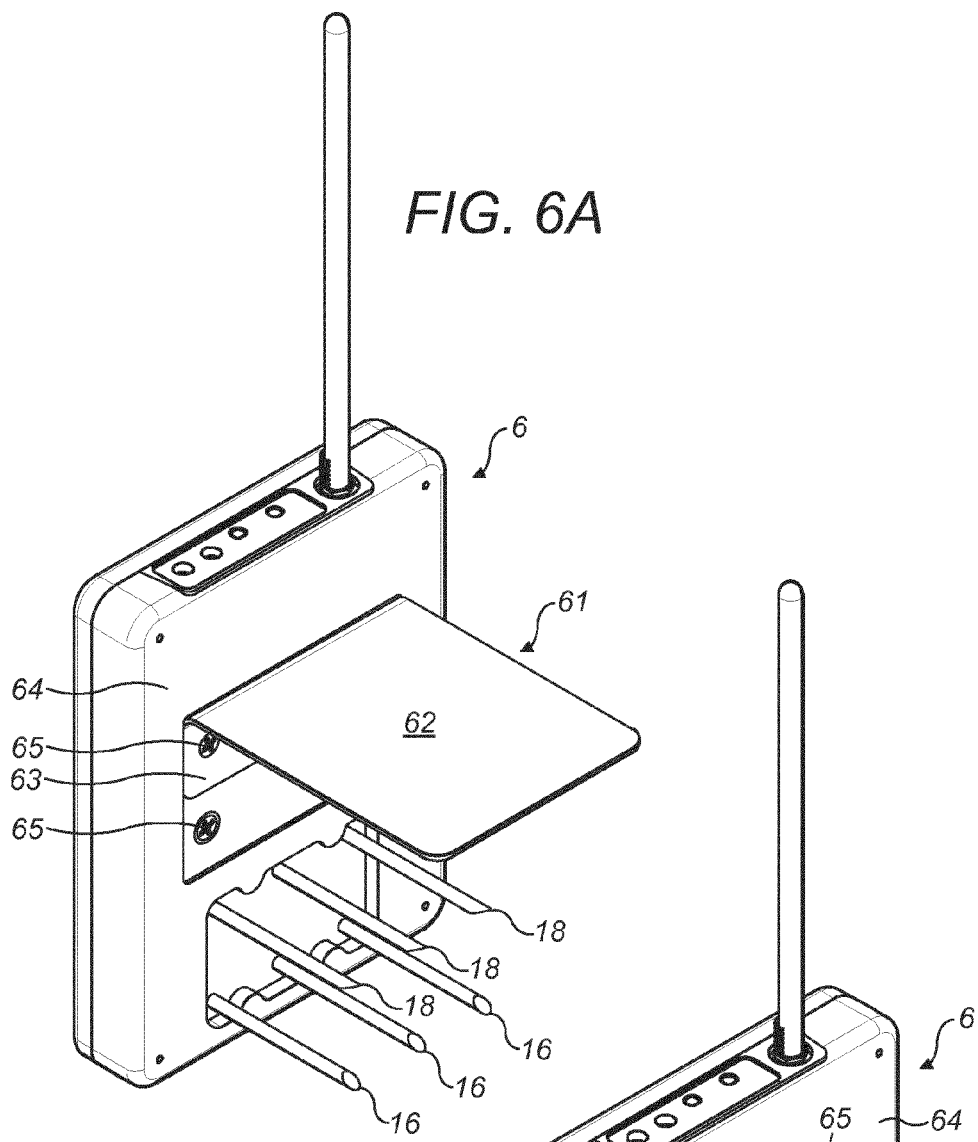
FIGS. 6A to 6C show an adjustable guide element arrangement for the present invention.
Figure 6B:
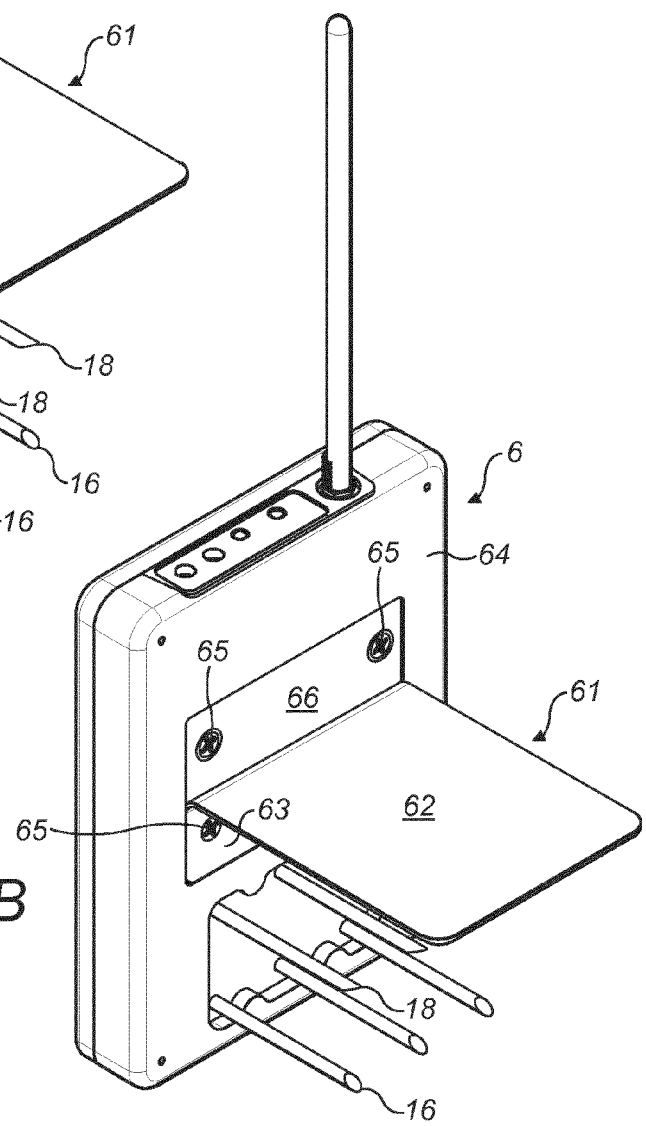
Figure 6C:
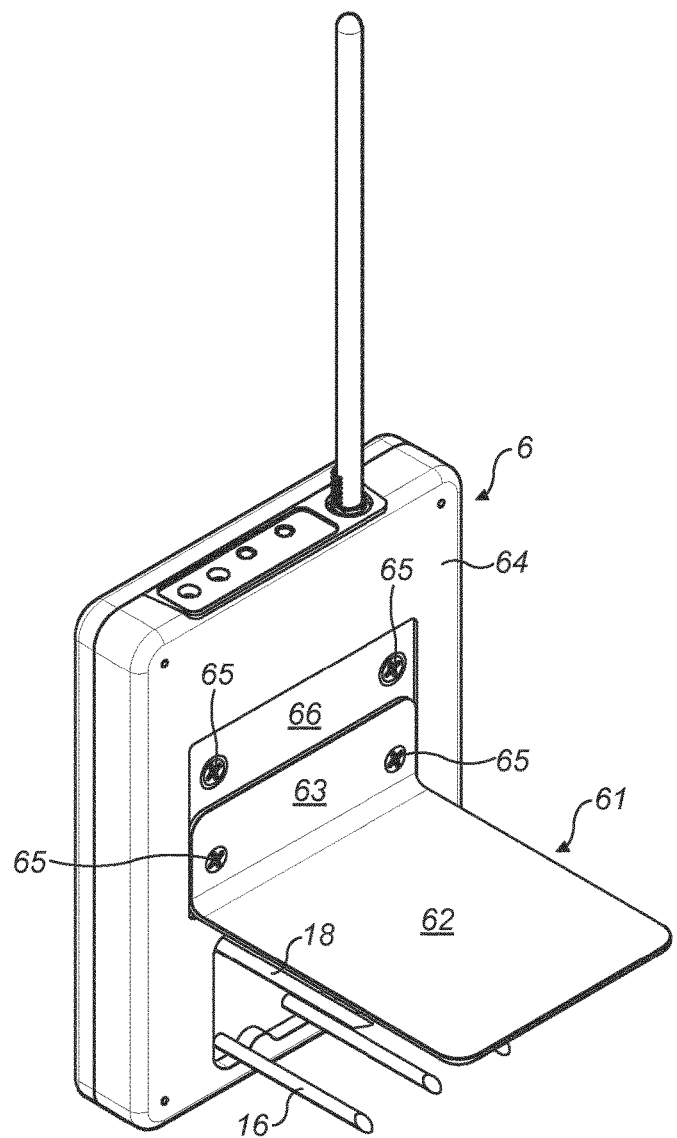
Figure 7A:
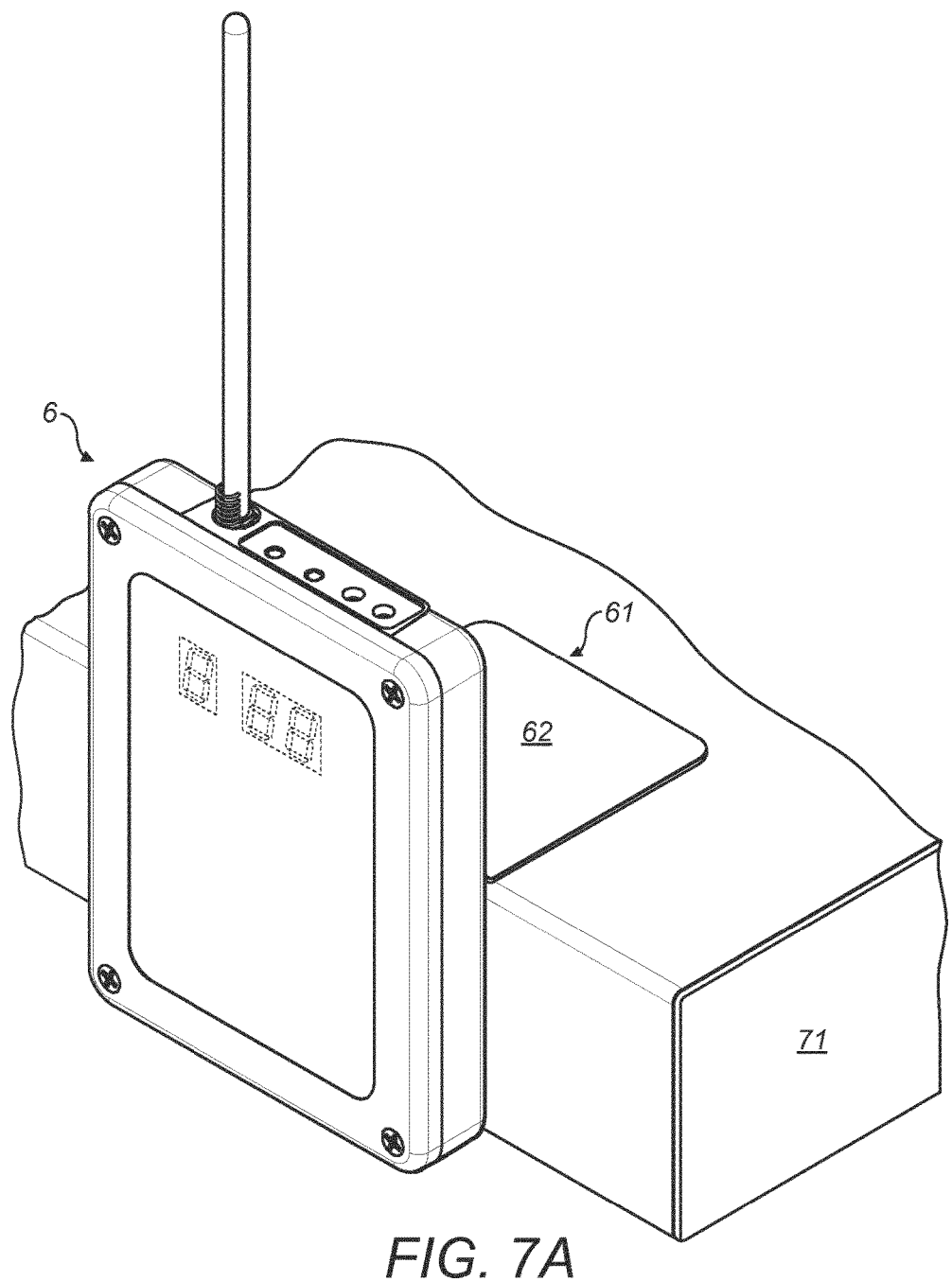
FIGS. 7A, 7B and 7C show the adjustable guide element arrangement of FIGS. 6A to 6C against a substrate.
Figure 7B:
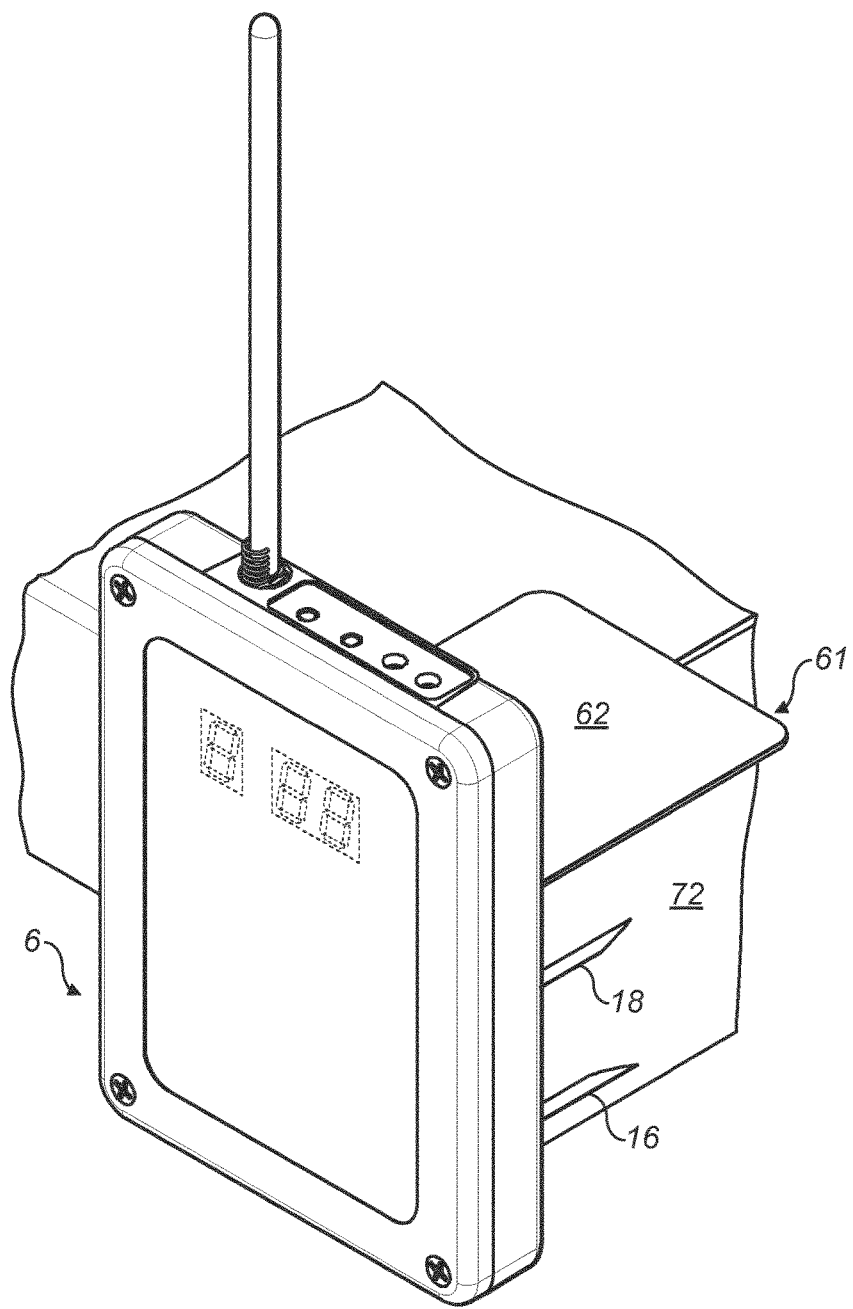
Figure 7C:
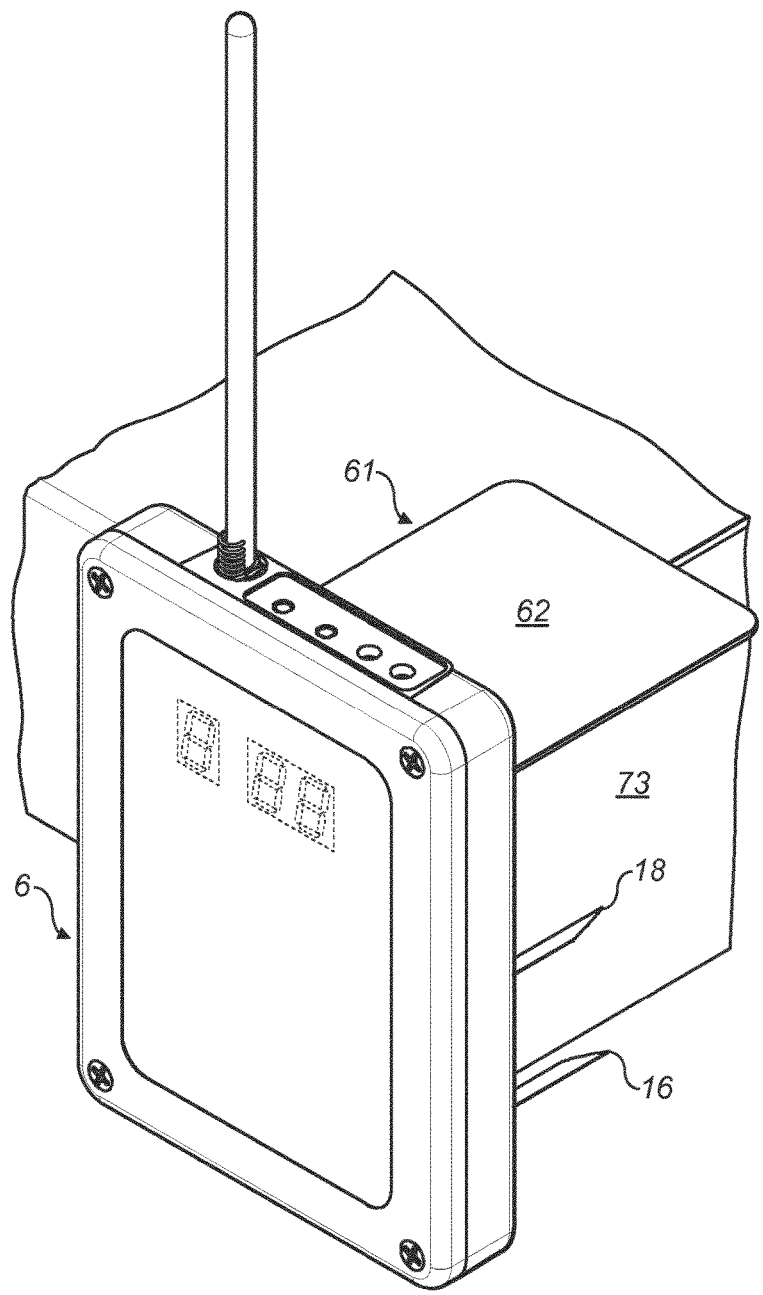

An example of such an arrangement is shown in FIGS. 6A to 6C. The arrangement comprises a guide element in the form of a guide plate 61 applied to a device 6 of the present invention. The guide plate 61 is shown in a first orientation in FIG. 6A, in which the guide plate is in an upper-most orientation relative to the probes 16 and 18. The guide plate comprises a guide section 62 and an attachment section 63. The attachment section can be applied to the main body 64 of the device at a plurality of selectable engagement points 65, here shown as a set of screws applied to a sub-set of an array of holes provided in the main body 64. By applying the guide element 61 at an upper set of holes as shown in FIG. 6A, a first, longer, distance can be maintained between the guide plate 62 and the probes 16, 18. By maintaining the orientation of the guide plate and moving it to a lower sub-set of screw holes 65, the guide plate can be held at an intermediate position relative to the probes 16, 18. This arrangement is illustrated in FIG. 6B. A further orientation can be used as illustrated in FIG. 6C, in which the orientation of the guide element is hanged, in this case by rotation through 180 degrees about an axis parallel to the probes 16, 18. By changing the orientation and using the set of holes nearest the probes, a further, smaller, distance between the probes and the guide element can be achieved. Depending upon the orientation of the main body 64, of the guide element, or of the holes 65 relative to the probes 16, 18, it will be appreciated that the guide element 61 can be adjusted to define a range of selectable set distances from the probes. Depending upon the placement of the guide element 61 above or below the probes, the distance of the probes from the top or bottom or a side or any surface of the substrate can be reliably and repeatably set. This can assist in obtaining more repeatable measurements of substrate conditions from the probes. It can be beneficial to maintain the probes at, or centred around, a mid-height of the slab in question. As specific examples, the orientation of FIG. 6A may be useful with a slab of height 10 cm. The arrangement of FIG. 6B may be used with a slab height of 7.5 cm. The orientation of FIG. 6C may be useful in slabs of height 7.5 cm, where a gutter covers the lower 2 cm of the slab, changing the apparent mid-height point of the slab height.

A blanking element or elements can be used to cover the set of holes 65 not being occupied by the attachment section 63. This may be provided in the form of a plate covering the whole area 66 around the holes 65 which are not being occupied by the attachment section 63. The blanking element and guide element 61 can be kept on the device 6 at all times during use, which means that the parts required for each configuration are always to hand for a user and the risk of losing parts during use is reduced. The blanking element or elements can also assist in maintaining the body 64 of the device 6 watertight, so that water or other dirt, or undesirable substances do not enter the body 64 of the device 6. If a blanking plate is used over all of area 66 around the unused holes of the device, it can also help to strengthen the body 64 of the device 66. It will be appreciated that the guide element can be useful in combination with, and also in isolation of, other features of the device 6 described herein, to maintain probes of a device for detecting plant growth conditions at a set distance from an edge of a substrate. The arrangement provides a plurality of configurations from one set of components and reduces manufacturing costs and simplifies assembly and use as compared to a system using multiple sets of guide elements for different requirements of guide element distance from the probes.

Variations and modifications to the embodiments described above will be apparent to the skilled person. Such variations and modifications may involve equivalent and other features which are already known and which may be used instead of, or in addition to, features described herein. Features that are described in the context of separate embodiments may be provided in combination in a single embodiment. Conversely, features which are described in the context of a single embodiment may also be provided separately or in any suitable sub-combination.

It should be noted that the term "comprising" does not exclude other elements or steps, the term "a" or "an" does not exclude a plurality, a single feature may fulfil the functions of several features recited in the claims and reference signs in the claims shall not be construed as limiting the scope of the claims. It should also be noted that the Figures are not necessarily to scale; emphasis instead generally being placed upon illustrating the principles of the present invention.

The invention claimed is:

1. A device for detecting plant growth conditions within a plant growth substrate, the device comprising:
    a first linear array of one or more probes for insertion into the substrate;
    a second linear array of one or more probes for insertion into the substrate, wherein the second linear array is located at a fixed distance from the first linear array;
    a control unit arranged to obtain a first measurement of at least one property of the substrate at a first substrate level from the first linear array of probes and a second measurement of the at least one property of the substrate at a second substrate level from the second linear array of probes,
    wherein the control unit is further arranged to combine the first and second measurements obtained at the first and second substrate levels to calculate at least one plant growth condition of the substrate as a function of the first and second measurements.

2. A device according to claim 1, wherein the at least one plant growth condition comprises water content.

3. A claim according to claim 2, wherein the at least one electrical property comprises capacitance.

4. A device according to claim 1, wherein the at least one plant growth condition comprises nutrient content.

5. A device according to claim 4, wherein the at least one electrical property comprises conductivity.

6. A device according to claim 1, wherein each linear array comprises three probes.

7. A device according to claim 1, wherein the probes are rotationally asymmetric at a distal end.

8. A device according to claim 7, wherein the probes are oblique truncated cylinders.

9. A device according to claim 7, wherein the probes have a non-uniform rotational orientation.

10. A device according to claim 1, further comprising an antenna for transmitting signals to a base station.

11. A device according to claim 1, further comprising a guide element adapted to engage with an edge of the substrate.

12. A device according to claim 11, wherein the guide element is adapted to engage with a bottom and/or top edge of the substrate.

13. A device according to claim 11 wherein the guide element is connected to the device by adjustable retaining means.

14. A device according to claim 13, wherein the adjustable retaining means are adapted to retain the guide element at a plurality of selectable positions relative to the probes.

15. A device according to claim 14, wherein the adjustable retaining means are adapted to retain the guide element at a plurality of selectable positions relative to the probes by using selectable different orientations of the guide element.

16. A device according to claim 15, wherein the adjustable retaining means comprises an array of first engagement points on one of a main body of the device and the guide element, and a set of corresponding second engagement points on the other of the main body and the guide element, for engaging sub-sets of the array of first engagement points.

17. A device according to claim 16, wherein the adjustable retaining means comprises an array of main engagement points on a main body of the device and a set of corresponding guide element engagement points on the guide element, for engaging sub-sets of the array of main engaging points.

18. A device according to claim 17, further comprising at least one blanking element for engaging at least one first engagement point which is not engaged by the second engagement points.

19. A plant growth system, comprising:
    a plant growth substrate comprising a slab;
    a device according to claim 1.

20. A plant growth system according to claim 19, wherein the probes of the device extend through a side wall of the slab.

21. A plant growth system according to claim 19, wherein the slab is a man-made vitreous fibre, MMVF, slab.

22. A device for detecting plant growth conditions within a plant growth substrate, the device comprising:
    a first linear array of one or more probes for insertion into the substrate;
    a second linear array of one or more probes for insertion into the substrate, wherein the second linear array is located at a fixed distance from the first linear array;
    a control unit arranged to obtain a first measurement of at least one property of the substrate from the first linear array of probes and a second measurement of the at least one property from the second linear array of probes,
    wherein at least one plant growth condition of the substrate is calculated using the first and second measurements,
    the device further comprising a guide element adapted to engage with an edge of the substrate, wherein the guide element is connected to the device by adjustable retaining means adapted to retain the guide element at a plurality of selectable positions relative to the probes.

23. A method for detecting plant growth conditions within a plant growth substrate, comprising:
    inserting probes of a detection device into the substrate, wherein the probes are arranged in a first linear array and a second array, the first linear array and the second linear array being located at a fixed distance from one another;
    obtaining a first measurement of at least one property of the substrate at a first substrate level from the first linear array of probes and obtaining a second measurement of the at least one property at a first substrate level from the second linear array of probes;
    combining the first and second measurements obtained at the first and second substrate levels; and
    calculating at least one plant growth condition of the substrate using the combined first and second measurements.

* * * * *